United States Patent
Minne

Patent Number: 6,063,047
Date of Patent: May 16, 2000

[54] MINIMAL ORTHESIS FOR THE TREATMENT OF OSTEOPOROSIS

[75] Inventor: Helmut W. Minne, Bad Pyrmont, Germany

[73] Assignee: Medi Bayreuth Weihermuller and Voigtmann GmbH & Co. KG, Bayreuth, Germany

[21] Appl. No.: 09/195,393

[22] Filed: Nov. 18, 1998

[30] Foreign Application Priority Data

Nov. 19, 1997 [DE] Germany ............. 297 20 475 U

[51] Int. Cl.⁷ ........................................... A61F 5/00
[52] U.S. Cl. ................................. 602/5; 602/19
[58] Field of Search .............. 602/5, 19; 128/869, 128/870

[56] References Cited

U.S. PATENT DOCUMENTS

| | | | |
|---|---|---|---|
| 709,055 | 9/1902 | Sheldon | 602/19 |
| 1,316,915 | 9/1919 | Meyer | 602/19 |
| 1,755,641 | 4/1930 | Foulke | 602/19 |
| 2,828,737 | 4/1958 | Hale | 602/19 |
| 3,945,376 | 3/1976 | Kuehnegger | 602/19 |

*Primary Examiner*—Michael A. Brown
*Attorney, Agent, or Firm*—Thomas R. Vigil

[57] ABSTRACT

Minimal orthesis for the treatment of osteoporosis comprising a rigid brace propping the spine as well as fastening structure for the brace guided around the truncus whereas the brace extends in a supporting manner essentially along the whole length of the spine, wherein the brace is provided with lower fastening belts for encompassing the truncus, the fastening belts being arranged at a height where they are not hindering abdominal respiration and the brace is provided with upper fastening belts which are guided in the way of rucksack straps over the shoulders and back underneath the arm pits so that they do not hinder thoracic respiration.

2 Claims, 2 Drawing Sheets

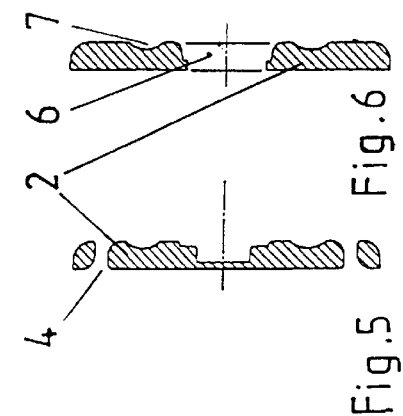
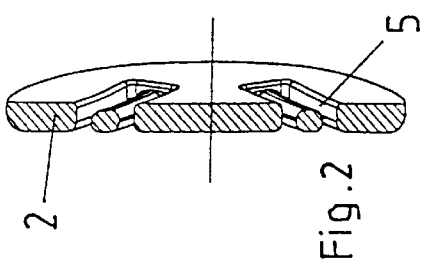
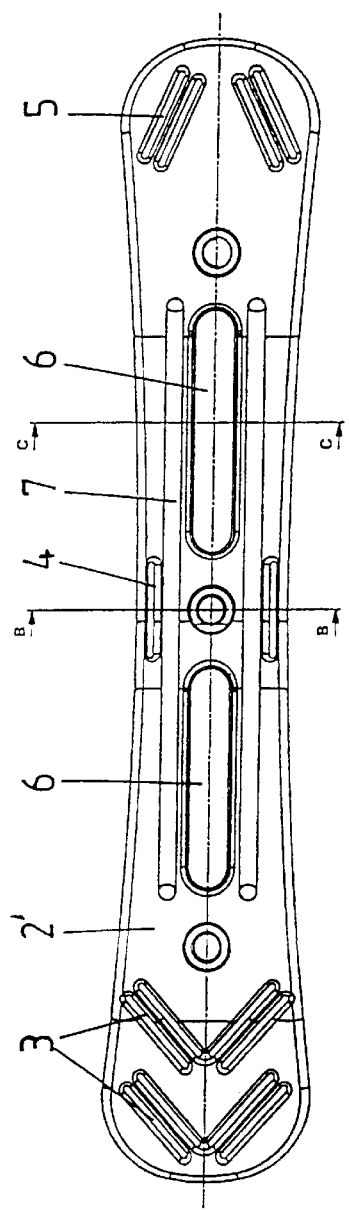
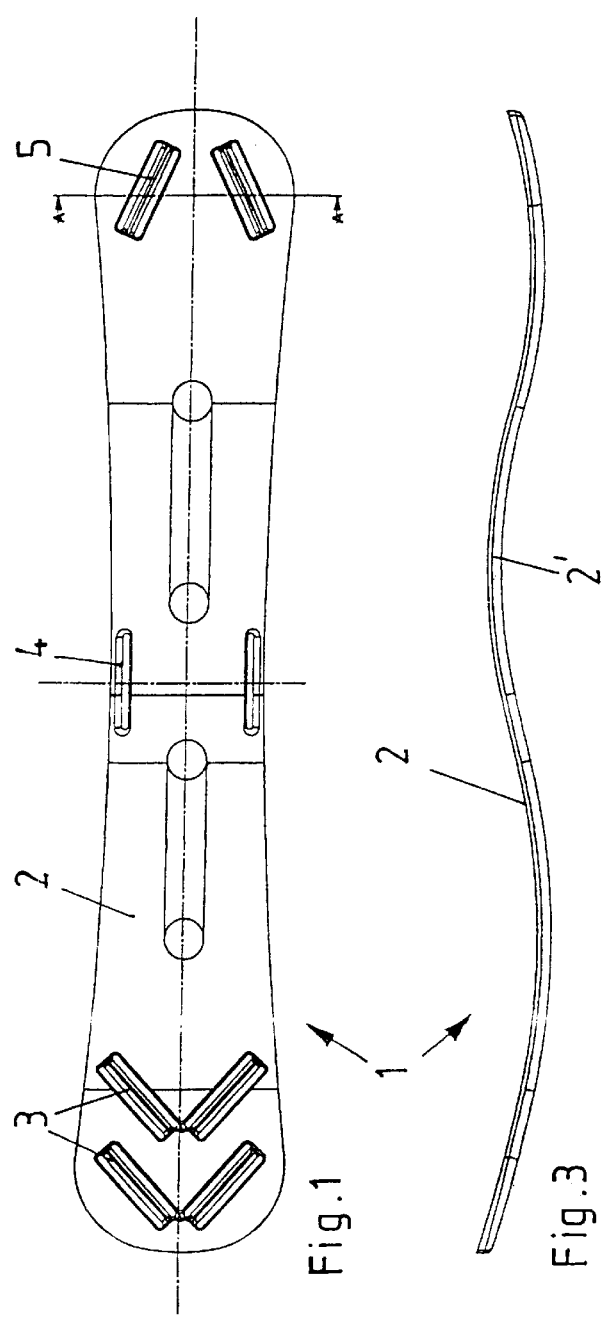

MINIMAL ORTHESIS FOR THE TREATMENT OF OSTEOPOROSIS

BACKGROUND OF THE INVENTION

1. Field of the Invention

The present invention relates to an orthesis for the treatment of osteoporosis comprising a rigid brace propping the spine as well as fastening structure for brace guided around the truncus.

2. Description of the Prior Art

Different types of orthesis for the treatment of osteoporosis are known. For example, German patent DE-C-39 28 628 which is sold under the name medi 3C, discloses a hyperextension orthesis with a basic plate, an abdominal rod extending from the basic plate downwards and which is provided with a padding for the symphysis, with webs extending laterally on both sides and provided with closing elements and with a breast rod extending upwards and provided with a slidable sternal padding. Another hyperextension orthesis is sold under the name medi 4C and does without abdominal and sternal rod and achieves an axial stabilization of thoracic and lumbar spine by means of a stable frame construction, whereas the truncus is kept from leaning forward underneath the clavicula. German patent DE-A-27 51 608 discloses an orthopedic support corset propping elastically the spine, wherein a brace comprising elastic members snuggles the spine and is fastened on the shoulders and the thighs by means of fastening structure.

The caving in of a vertebra is a typical late complication of osteoporosis. The deformation of the vertebra leads to misalignments of the facet articulations of the vertebrae, malfunctions of tendons, ligaments and muscles. They are the origin of chronic pain and disability in every day life.

It is the purpose of an orthesis to straighten up the spine in order to relieve the compressed vertebral body and thereby the strained and aching periost, to improve the function of the facet articulations and to thereby avoid durable articulation defects. This procedure improves the treatment possibilities after fresh fracture and in the case of chronic deformation of the spine. The present invention makes such a straightening possible by modeling the kyphotic spine on an orthesis snuggling the back from behind. The orthesis is able to prevent pain and to improve mobilization.

All the ortheses used up to now and aimed at achieving the treatment goal are constricting (elastic body-belts) or exert pressure onto structures used as abutments for the straightening of the spine. This hems in the patients, hinders them in their movements in a way that is often unbearable and is the reason why these remedial accessories are not used as much as desired. It thus normally represents a hindrance for an adequate use of a therapeutic attempt which in itself is desirable.

The present invention is able, on one side, to straighten the spine as desired but it does it due to its construction without hindering thoracic and abdominal respiration and without restricting the mobility in the shoulder and arm area.

This improves the acceptance of this new orthesis by the patients and at the same time their treatability in an impressive manner. The treatability of patients suffering from osteoporosis and from the caving in of vertebrae is improved.

To sum up, it may be said that the known solutions restrict thoracic and abdominal respiration as well as the mobility in the shoulder and arm area.

SUMMARY OF THE INVENTION

An object of the present invention is therefore to provide a minimal orthesis for the treatment of osteoporosis which minimizes the restriction of thoracic and abdominal respiration as well as of the mobility in the shoulder and arm area.

The solution of this object is obtained by providing a rigid brace with fastening structure for the brace guided around the truncus wherein the brace extends in a supporting manner essentially along the whole length of the spine, the brace being provided with lower fastening belts for encompassing the truncus, the fastening belts being arranged at a height where they are not hindering abdominal respiration, and the brace being provided with upper fastening belts which are guided in the way of rucksack straps over the shoulders and back underneath the arm pits so that they do not hinder thoracic respiration.

According to the invention, a minimal orthesis for the treatment of osteoporosis comprising a rigid brace propping the spine as well as fastening structure for the brace guided around the truncus is characterized in that the brace extends in a supporting manner essentially along the whole length of the spine, that the brace is provided with lower fastening belts for encompassing the truncus, that fastening belts are arranged at a height where they are not hindering abdominal respiration and that the brace is provided with upper fastening belts which are guided in the way of rucksack straps over the shoulders and back underneath the arm pits so that they do not hinder thoracic respiration.

The brace preferably extends in width over less than half the body width and in height from the tailbone up to the first cervical vertebra so that the leaning forward and the flexibility of the spine is propped in the area of the lumbar spine and of the thoracic spine. Lateral leaning and the mobility in the shoulder and arm area are hardly restricted.

BRIEF DESCRIPTION OF THE DRAWINGS

FIG. 1 shows the front side of a brace of a minimal orthesis.

FIG. 2 shows an enlarged section along the line A—A of FIG. 1.

FIG. 3 shows a lateral view of the brace of FIG. 1.

FIG. 4 shows the back side of the brace of FIG. 1.

FIG. 5 shows an enlarged section along the line B—B of FIG. 4.

FIG. 6 shows an enlarged section along the line C—C of FIG. 4.

DESCRIPTION OF THE PREFERRED EMBODIMENTS

Figure 7:
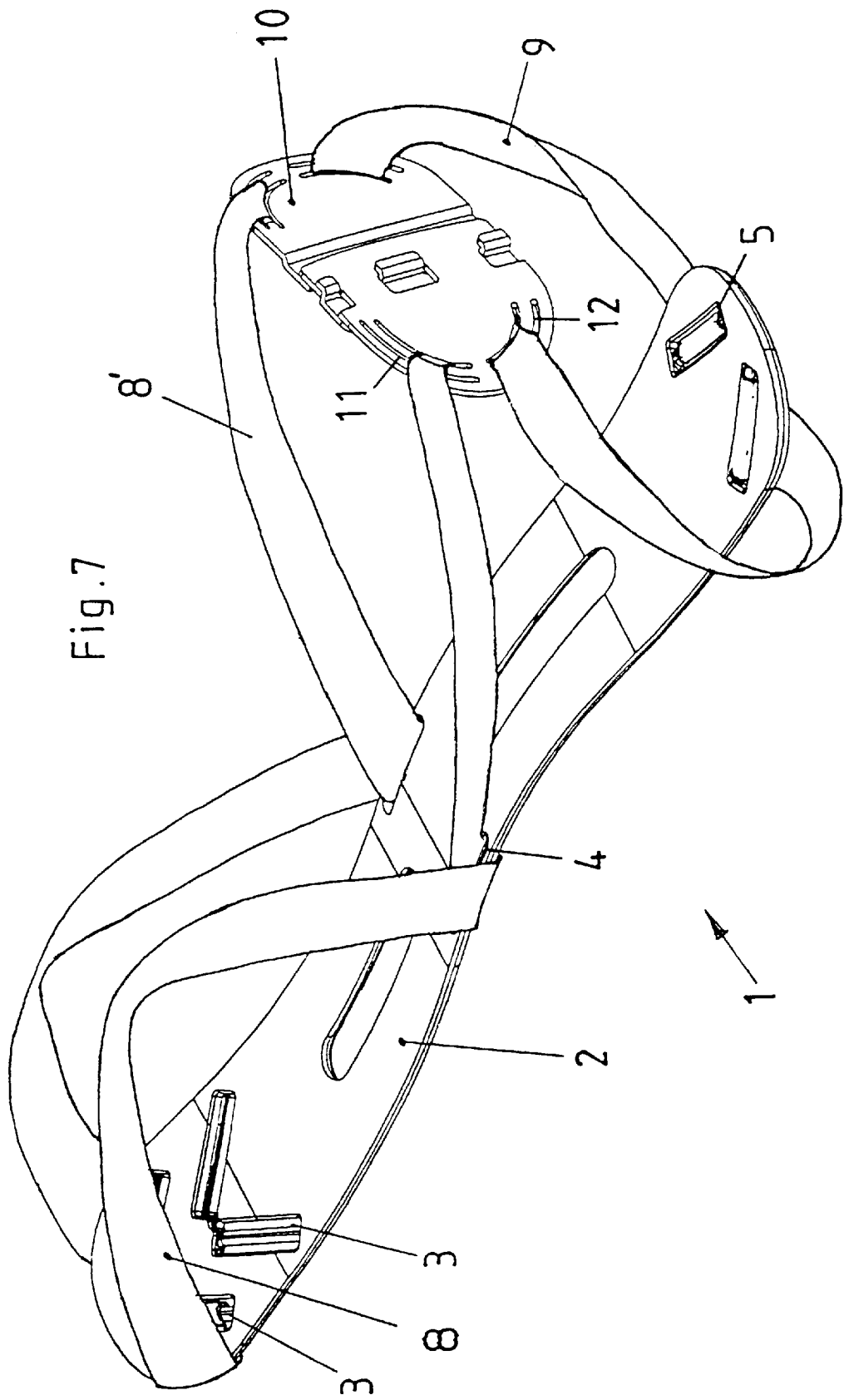
FIG. 7 shows a perspective view of a minimal orthesis composed of brace and fastening structure.

The brace 1 according to FIGS. 1–6 is a lengthy, modeled plastic part that is given the curves corresponding to the spinal anatomy as may be seen in FIG. 3, wherein the brace is extending from the tailbone to the first cervical vertebra. The brace is provided with upper slanted fastening slots 3 for shoulder straps, central, lateral reversing slots 4 for the shoulder straps and slanted lower fastening slots 5 for the fastening of pelvic belts. The fastening slots 3 and 5 are arranged in couples on both sides alongside a separating web, whereas the upper fastening slots 3 are provided twice with a spacing-in between in order to adapt to different body sizes. The brace is made of two halves 2, 2' bonded together.

Openings 6 are provided to minimize its weight and longitudinal grooves 7 improve its stability.

The fastening structure arranged on the brace 1 as shown in FIG. 7. A shoulder strap 8 is fastened laterally in each one of the upper fastening slots 3, the shoulder strap being guided towards the front from the rear side of the brace. The shoulder straps 8 extend downwards like rucksack straps, being reversed in the lateral reversing slots 4 before they are brought together with a lower belt section 8' to an abdominal padding 10 on which they are fastened in upper fastening slots 11. The abdominal padding 10 comprises two halves that may be locked together or taken apart and also provided are lower fastening slots 12 for the fastening of pelvic belts 9 that are, on their lower ends, fastened in the lower fastening slots 5. The length of the belts may be adjusted to the body size.

I claim:

1. Minimal orthesis for the treatment of osteoporosis comprising a rigid brace propping the spine as well as fastening means for said brace guided around the truncus characterized in that said brace (1) is elongate, has a curved shape following the spine and extends in a supporting manner substantially the whole length of the spine from and including the tailbone to and including the first cervical vertebra, said brace (1) is provided with first, lower fastening belts (9) for encompassing the truncus and then extending to an abdominal padding (10), said fastening belts being arranged at a height where they do not hinder abdominal respiration, and said brace (1) is provided with second, upper fastening belts (8) which are guided in the way of rucksack straps over the shoulders and back underneath the arm pits so that they do not hinder thoracic respiration and then into reversing slots (4) in said brace (1), and from there around the truncus to the abdominal padding (10).

2. Minimal orthesis for the treatment of osteoporosis according to claim 1, characterized in that said brace (1) extends in width over less than half the body width.

* * * * *